United States Patent
Limon et al.

(10) Patent No.: US 6,585,747 B1
(45) Date of Patent: Jul. 1, 2003

(54) INTERDIGITATING POLYMERIC ENDCAP FOR ENHANCED STENT RETENTION

(75) Inventors: Timothy A. Limon, Cupertino, CA (US); Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/548,802

(22) Filed: Apr. 14, 2000

(51) Int. Cl.[7] ............................................. A61B 17/34
(52) U.S. Cl. ....................................... 606/198; 606/108
(58) Field of Search ................... 606/108, 198, 606/195, 194, 191; 604/96.01, 104, 264

(56) References Cited

U.S. PATENT DOCUMENTS

| | | | |
|---|---|---|---|
| 2,701,559 A | | 2/1955 | Cooper |
| 4,199,646 A | | 4/1980 | Hori et al. |
| 4,733,665 A | | 3/1988 | Palmaz |
| 4,880,683 A | | 11/1989 | Stow |
| 4,950,227 A | | 8/1990 | Savin et al. |
| 5,078,720 A | | 1/1992 | Burton et al. |
| 5,100,429 A | | 3/1992 | Sinofsky et al. |
| 5,108,416 A | | 4/1992 | Ryan et al. |
| 5,156,911 A | | 10/1992 | Stewart |
| 5,158,548 A | | 10/1992 | Lau et al. |
| 5,242,399 A | | 9/1993 | Lau et al. |
| 5,292,331 A | * | 3/1994 | Boneau ................. 606/198 |
| 5,344,426 A | | 9/1994 | Lau et al. |
| 5,360,401 A | | 11/1994 | Turnland |
| 5,387,450 A | | 2/1995 | Stewart |
| 5,403,341 A | * | 4/1995 | Solar ................... 606/198 |
| 5,412,035 A | | 5/1995 | Schmitt et al. |
| 5,445,646 A | | 8/1995 | Euteneuer et al. |
| 5,514,154 A | | 5/1996 | Lau et al. |
| 5,571,135 A | | 11/1996 | Fraser et al. |
| 5,653,691 A | | 8/1997 | Rupp et al. |
| 5,720,726 A | | 2/1998 | Marcadis et al. |
| 5,759,474 A | | 6/1998 | Rupp et al. |
| 5,810,871 A | | 9/1998 | Tuckey et al. |
| 5,830,217 A | | 11/1998 | Ryan |
| 5,836,965 A | | 11/1998 | Jendersee et al. |
| 5,893,852 A | | 4/1999 | Morales |
| 5,911,752 A | * | 6/1999 | Dustrude et al. ........ 604/96.01 |
| 5,957,930 A | * | 9/1999 | Vrba ..................... 623/1.11 |
| 5,968,069 A | * | 10/1999 | Dusbabek et al. ...... 604/96.01 |
| 5,976,155 A | | 11/1999 | Foreman et al. |
| 5,980,530 A | * | 11/1999 | Willard et al. ............ 606/195 |
| 5,989,280 A | * | 11/1999 | Euteneuer et al. ......... 623/1.1 |
| 6,027,510 A | | 2/2000 | Alt |
| 6,051,021 A | | 4/2000 | Frid |
| 6,059,810 A | | 5/2000 | Brown et al. |
| 6,068,634 A | * | 5/2000 | Lorentzen Cornelius et al. ..................... 606/198 |

(List continued on next page.)

FOREIGN PATENT DOCUMENTS

| | | |
|---|---|---|
| EP | 0 834 293 A1 | 4/1998 |
| EP | 0 974 315 | 1/2000 |
| FR | 2 753 907 A1 | 10/1996 |
| WO | WO 95/33422 | 12/1995 |
| WO | WO 98/07390 | 2/1998 |

*Primary Examiner*—Brian L. Casler
*Assistant Examiner*—Kevin C. Sirmons
(74) *Attorney, Agent, or Firm*—Fulwider Patton Lee & Utecht, LLP

(57) ABSTRACT

A stent deployment assembly with a novel endcap is disclosed. The endcap includes a tapered member having a first end and a second end. The first end and the second end each have an aperture therethrough. The tapered member has a pre-expanded condition and an expanded condition. The first end of the tapered member is positioned to interdigitate with an end of a stent mounted on a catheter when the tapered member is in the pre-expanded condition, and the first end is not positioned overlying the stent. The endcap prevents the stent from catching on calcium deposits or foreign objects during navigation through the vasculature. Furthermore, the endcap prevents unwanted migration of the stent with respect to the catheter.

2 Claims, 3 Drawing Sheets

U.S. PATENT DOCUMENTS

| | | | |
|---|---|---|---|
| 6,077,273 A | * | 6/2000 | Euteneuer et al. .......... 606/108 |
| 6,086,610 A | | 7/2000 | Duerig et al. |
| 6,099,559 A | | 8/2000 | Nolting |
| 6,123,712 A | | 9/2000 | Di Caprio et al. |
| 6,159,227 A | | 12/2000 | Di Caprio et al. |
| 6,270,504 B1 | * | 8/2001 | Lorentzen Cornelius et al. .......... 606/108 |
| 6,325,814 B1 | * | 12/2001 | Euteneuer et al. .......... 606/108 |
| 6,371,962 B1 | * | 4/2002 | Ellis et al. |
| 2001/0016753 A1 | | 8/2001 | Caprio et al. |

* cited by examiner

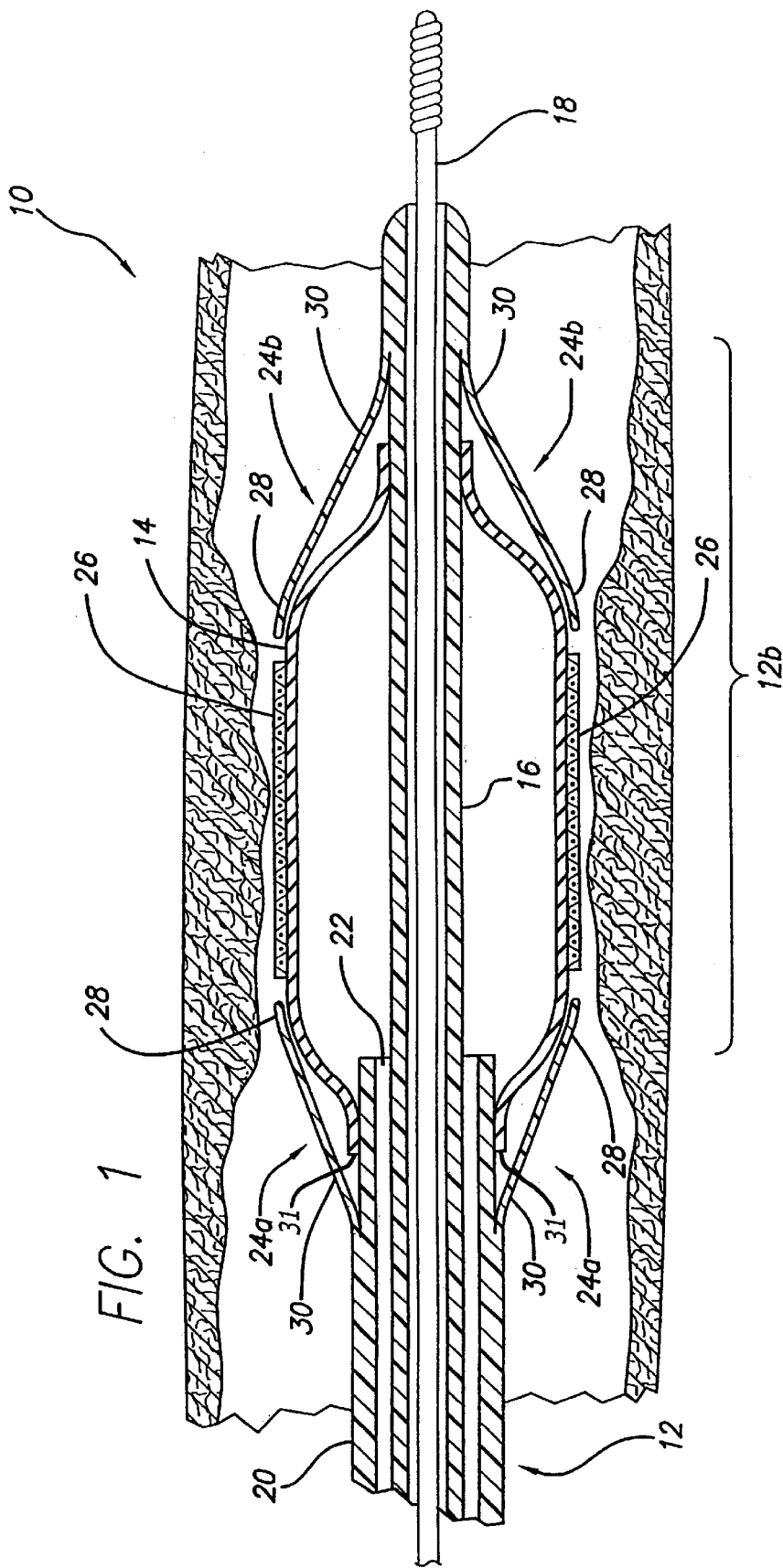

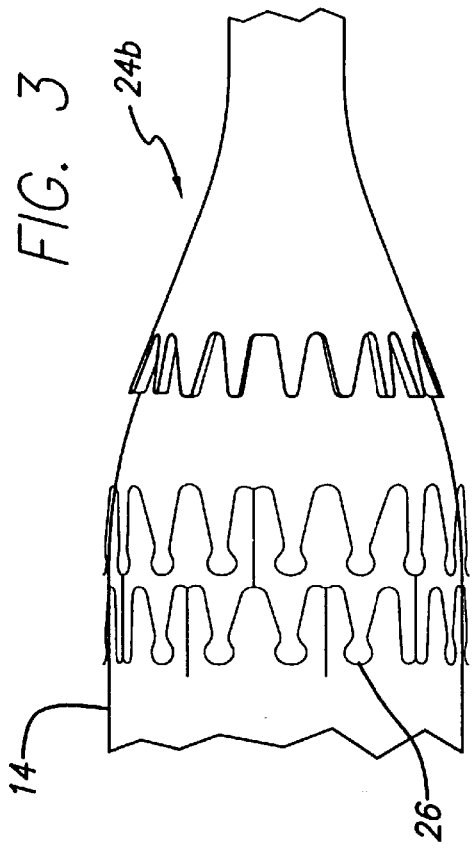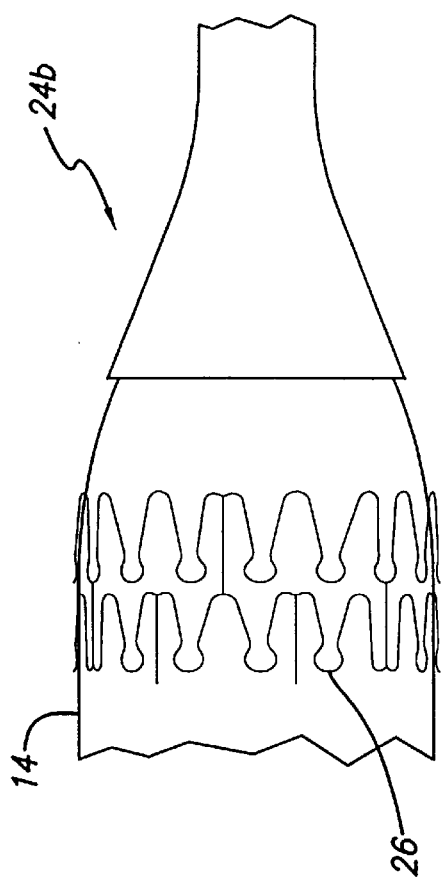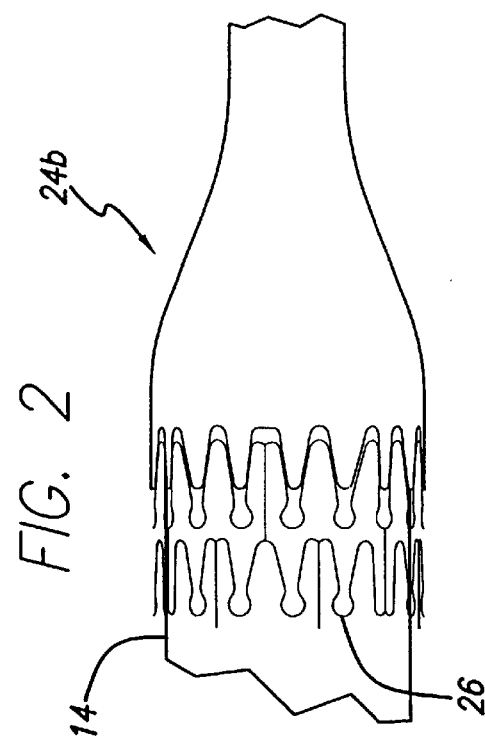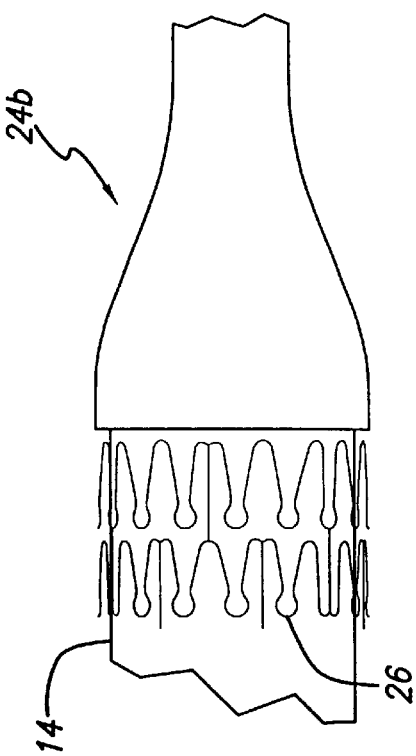

INTERDIGITATING POLYMERIC ENDCAP FOR ENHANCED STENT RETENTION

BACKGROUND OF THE INVENTION

The present invention relates in general to the delivery of stents into a body lumen, such as a blood vessel, to maintain the patency thereof. More particularly, the present invention relates to endcaps that are used in conjunction with the delivery of stents within a body lumen.

In a medical procedure known as percutaneous transluminal coronary angioplasty (PTCA), a balloon catheter is used to dilate the lumen of a coronary artery which has become narrowed or restricted due to the accumulation of atherosclerotic plaque along the artery wall. In the PTCA procedure, a balloon catheter is advanced through the vasculature to the stenosis and the balloon is inflated to radially compress the atherosclerotic plaque against the inside of the artery wall. The balloon is then deflated so that the dilation catheter can be removed and blood flow resumed through the dilated artery.

Occasionally, the inflation of the balloon within the artery lumen will dissect either the stenotic plaque or the intima of the blood vessel or both. Subsequent to the balloon being deflated and removed, blood can flow between the arterial wall and the dissected lining thereby constricting the flow passage or causing a section of the dissected lining, commonly called an "intimal flap," to be forced into the flow passageway. In the event of partial or total occlusion of an artery by a dissected arterial lining, the patient is put in an extremely dangerous situation requiring immediate medical attention.

Another problem that frequently arises after an angioplasty procedure is the appearance of a restenosis at or near the site of the treated artery. The restenosis may appear due to the accumulation of additional atherosclerotic plaque but is typically due to neointimal proliferation as a result of vessel injury and foreign body response. When restenosis appears, the treated patient may require an additional angioplasty procedure or other treatment such as by-pass surgery, if an additional angioplasty procedure is not warranted.

Due to the problems caused by dissections of the arterial lining or the appearance of restenosis, much research has been performed on ways to maintain the patency of an artery after the angioplasty procedure is completed. In recent years, expandable endoprosthetic devices, commonly called "stents," have gained widespread acceptance as a means to support the arterial walls and maintain the patency of a treated vessel. Stents are generally cylindrically shaped intravascular devices that are placed within a damaged artery to hold it open and maintain unimpeded blood flow. Stents prevent dissected arterial linings from occluding an artery by pressing the dissected tissue against the arterial wall until natural healing results in the re-securing of the dissected tissue to the arterial wall. Compared to balloon angioplasty, stents improve short term outcome by preventing elastic recoil and long term outcome by a reduction in positive vessel remodeling.

As with all interventional techniques, the use of stents requires particular training and technique for optimum placement in the coronary vasculature. There are many measures of the performance of a stent delivery system that affect its ease of use and clinical utility. Low profile, flexibility and good push characteristics affect the ability of the stent to cross the lesion. It is critical that the stent stay on the delivery system until it is at the desired site. During placement, stents experience frictional forces as they negotiate tortuous vasculature. Furthermore, stents often have to cross calcified lesions and already deployed stents where there is the chance of catching a strut. Sometimes the stent cannot be deployed for a variety of reasons. In these instances, the stent must be able to be pulled back into the guiding catheter without being stripped off the balloon. Despite care in the handling of stents currently, stents do become dislodged from the delivery systems or damaged and require removal. The consequences of losing a stent can be life threatening and can require immediate surgery.

What has been needed and heretofore unavailable is a device that provides a means for preventing longitudinal movement of the stent off of the balloon. The device should additionally make it more difficult for the stent edges to catch on other objects as the stent is moved within the vasculature. Additionally, the device should exhibit a relatively low profile for delivery through the vasculature. The present invention satisfies these needs and others.

As used herein, the terms "proximal," "proximally" and "proximal direction" when used with respect to the invention are intended to mean moving away from or out of the patient, and the terms "distal," "distally" and "distal direction" when used with respect to the invention are intended to mean moving toward or into the patient. These definitions will apply with reference to apparatus, such as catheters, guide wires, stents and the like.

SUMMARY OF THE INVENTION

The invention provides for a stent deployment system for delivering a stent within a body lumen. The system includes a novel endcap that serves many important functions.

In one aspect of the invention, there is provided an endcap, including a tapered member having a first end and a second end. The first end and the second end each have an aperture therethrough. The tapered member has a pre-expanded condition and an expanded condition. The first end of the tapered member is positioned against an end of a stent mounted on a catheter when the tapered member is in the pre-expanded condition. The first end of the endcap interdigitates or meshes with respect to an end of the stent.

In another aspect of the invention, there is provided a stent deployment system for delivery of a stent within a body lumen. The system includes a catheter for delivering and implanting a stent. The distal end of the catheter includes an expandable member upon which a stent is mounted. An endcap is positioned in apposition with an end of the stent. The endcap is in the shape of a tapered member including a first end and a second end, the first end and the second end each having an aperture therethrough. The tapered member has a pre-expanded condition and an expanded condition. The first end of the tapered member is positioned against an end of the stent when the tapered member is in the pre-expanded condition. The first end of the end cap interdigitates with respect to an end of the stent. The endcap decreases the deflation time of the expandable member and assists in folding of the expandable member upon deflation. The endcap also holds the stent on the expandable member before inflation.

In yet another aspect of the invention, there is provided a stent deployment system for delivery of a stent within a body lumen. The system includes a catheter having an expandable member. A stent is mounted on the expandable member. A means is provided for retaining the stent on the expandable member. The means for retaining interdigitates with the stent and has a pre-expanded condition and an expanded condition. A first end of the means for retaining is positioned against an end of the stent when the means for retaining is in the pre-expanded condition.

In a further aspect of the invention, there is provided a method of forming an endcap. A catheter is provided having a proximal end and a distal end, wherein the distal end has an expandable member and a stent is mounted on the expandable member. A liquid is introduced onto the expandable member distal to the stent. The liquid is allowed to harden such that an interdigitating endcap is formed.

In a still further aspect, there is provided a method of forming an endcap, utilizing a tapered cylindrical mold and a catheter having a proximal end and a distal end. The distal end of the catheter has an expandable member and a stent is mounted on the expandable member. A liquid is introduced into the mold. The liquid is allowed to harden such that an endcap is formed. The endcap is applied to the catheter distal to the stent with an adhesive.

The stent delivery system can be used to accurately deliver a stent to a desired location within a patient's vasculature system or other body lumen by preventing the stent from getting caught on calcium deposits or foreign objects. The system further prevents unwanted migration of the stent from the expandable portion of the catheter. The present invention can be used to treat various vessels including but not limited to the coronary arteries. Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a longitudinal cross-sectional view of a delivery assembly of the present invention.

FIG. 2 is a perspective view of an interdigitating endcap of the present invention, shown in a slightly expanded condition.

FIG. 3 is a perspective view of the interdigitating endcap of FIG. 2, shown during expansion.

FIG. 4 is a perspective view of a non-interdigitating endcap of the present invention, shown in a slightly expanded condition.

FIG. 5 is a perspective view of the non-interdigitating endcap of FIG. 4, shown during expansion.

DETAILED DESCRIPTION OF THE PREFERRED EMBODIMENTS

Figure 6:
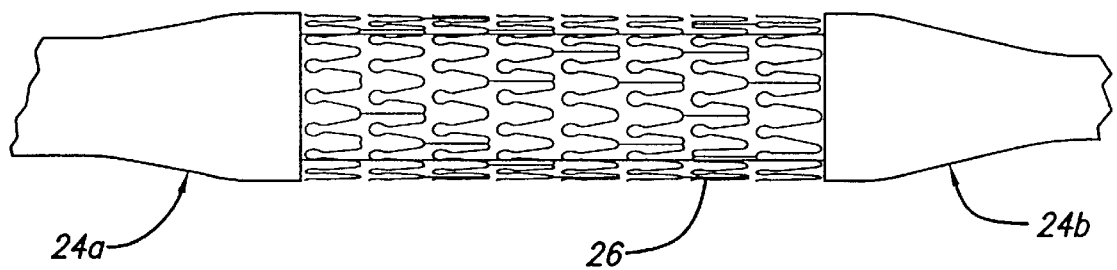
FIG. 6 is an elevational view of a delivery assembly of the present invention, before any inflation of the balloon.

As shown in the exemplary drawings wherein like reference numerals indicate like or corresponding elements among the figures, the present invention includes a stent deployment system for treating various vessels, such as coronary arteries, in the body.

Typically, a stent is delivered and deployed by crimping the stent onto the distal end of a balloon catheter and slidably disposing the catheter and stent within a guide catheter that has been delivered into a vessel. Once the balloon catheter and stent are advanced to the desired location within the vessel, the balloon is inflated, thereby causing the stent to expand against the vessel wall.

As mentioned previously, it is critical that the stent stay on the delivery system until it is positioned at the treatment site. During placement, stents experience frictional forces as they negotiate tortuous vasculature. Furthermore, stents often have to cross calcified lesions and already deployed stents where there is the chance of catching a strut. Sometimes the stent cannot be deployed for a variety of reasons. In these instances, the stent must be able to be pulled back into the guiding catheter without being stripped off the balloon. Consequently, a device that provides a means for preventing longitudinal movement of the stent off of the balloon would be of use in treating patients. The device should further make it more difficult for the stent edges to catch on other objects as the stent is moved within a body lumen.

Figure 7:
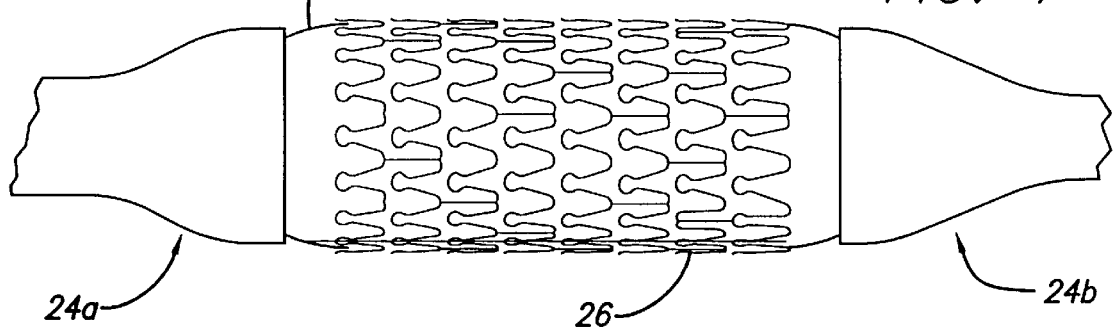
FIG. 7 is an elevational view of the delivery assembly of FIG. 6, depicting the balloon in a partially inflated condition.
Figure 8:
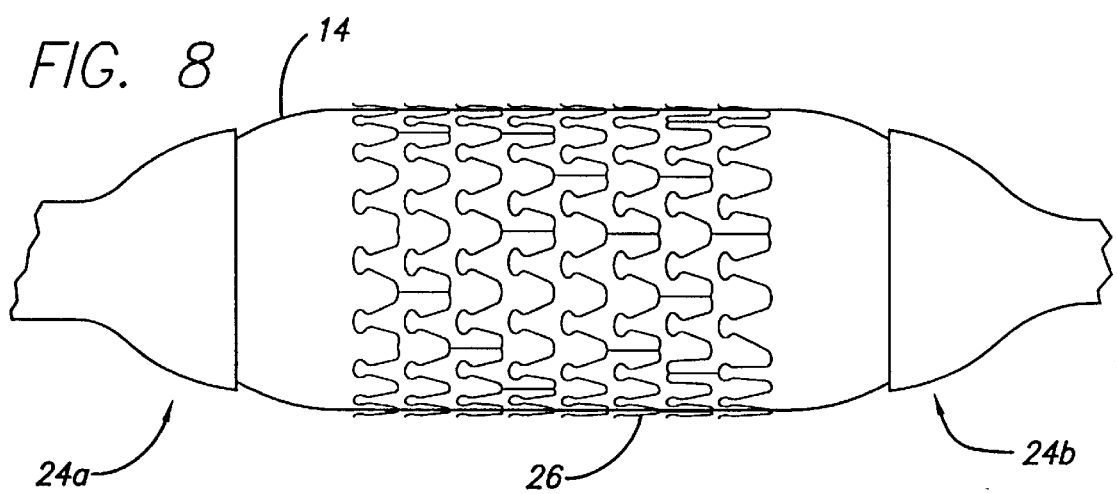
FIG. 8 is an elevational view of the delivery assembly of FIG. 7, depicting the balloon in a partially inflated condition, approaching full inflation.
Figure 9:
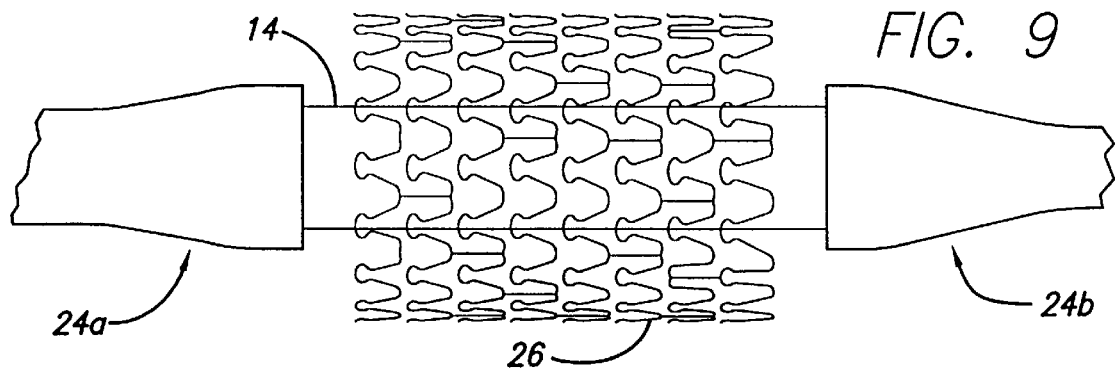
FIG. 9 is an elevational view of the delivery assembly of FIG. 7, depicting the stent in a fully expanded condition with the balloon deflated.

FIGS. 1–9 illustrate an exemplary stent deployment system that embodies features of the present invention. Referring to FIG. 1, stent deployment system 10 is depicted for delivery of a stent within a body lumen. The system includes balloon catheter 12 having a proximal end and distal end 12b. The distal end is configured for mounting a stent thereon. The distal end of the balloon catheter includes expandable member 14, such as a balloon, depicted in a partially expanded condition. The balloon catheter has inner member 16. The inner member is an elongate tubular member configured to receive guide wire 18 which can slide through the catheter. An outer member 20 is an elongate tubular member having a diameter greater than that of the inner member. The inner member is positioned within the outer member such that there is a small space between the two members. This space serves as inflation lumen 22. The inflation lumen extends from within the interior of the expandable member to a point somewhere proximally down the length of the balloon catheter, whereupon the lumen exits the catheter. The delivery catheter can be constructed from polyethylene ("PE tube") or other suitable materials.

A novel means for retaining stent 26 on expandable member 14, or first endcap 24a, is positioned in apposition with a proximal end of stent 26, shown in a partially expanded condition. The endcap is also useful for preventing longitudinal movement of a stent off of a catheter, and for preventing the stent from catching on objects. The stent may be of any suitable kind. In one embodiment the stent is of the balloon-expandable type and is made of stainless steel. The stent is crimped onto expandable member 14 when the expandable member is deflated, as is known in the art.

The first endcap 24a is in the shape of a tapered member including first end 28 and second end 30, the first end and the second end each having an aperture therethrough. The tapered member has a pre-expanded condition and an expanded condition, and is shown in FIG. 1 in the process of expansion. The diameter of the first end of the endcap in the pre-expanded condition is smaller than the diameter of the first end of the endcap in the expanded condition.

The first end 28 of the tapered member, or first endcap 24a, is positioned against an end of stent when the tapered member is in the pre-expanded condition. The first end of the tapered member is not positioned overlying the stent. Instead, the first end of the tapered member is positioned substantially flush with an end of the stent to provide for a lower delivery profile. The outer diameter of the first end of the endcap in the pre-expanded condition is approximately equal to or slightly larger than the outer diameter of the stent when the stent is crimped. A good juxtapositioning of the endcaps to the ends of stent 26 will keep the stent from migrating.

In keeping with the invention, second endcap 24b similarly is in the shape of a tapered member including first end 28 and second end 30, the first end and the second end each having an aperture therethrough. The tapered member has a pre-expanded condition and an expanded condition, and is shown in FIG. 1 in the process of expansion. The endcaps are elastomeric so that they can be expanded and then later, due to their memory, contract. Designing the endcaps from a soft material ensures that they do not interfere with the expansion of expandable member 14. Furthermore, the use of a soft material is required to preserve the longitudinal flexibilty of the device. The use of a stiff endcap could create an inflexible section in catheter 12 that could make passage though tortuous regions of the vasculature more difficult.

The first end 28 of the tapered member, or second endcap 24b, is positioned against an end of stent 26 when the tapered member is in the pre-expanded condition. The first end of the tapered member is not positioned overlying the stent. Instead, the first end of the tapered member is positioned substantially flush with an end of the stent to provide for a lower delivery profile. The outer diameter of the first end of the endcap in the pre-expanded condition is approximately equal to or slightly larger than the outer diameter of the stent when the stent is crimped. Consequently there is a smooth transition between the endcap and the stent. The endcaps 24a, 24b taper down away from the stent to meet catheter 12 to provide for a sleek catheter profile that is easily advanced through the vasculature. The second ends of the endcaps can be attached to the catheter on or proximate weld joints 31 where the expandable member contacts the catheter as shown in FIG. 1. Alternatively, the second ends of the endcaps can be attached to the shoulders of the expandable member. The endcaps are capable of withstanding axial loads during navigation through tortuous vasculature. The endcaps can have a range of thickness, and preferably a thickness of between 1 and 10 mils.

The endcaps are especially useful with stepped balloons, which are known in the art. The advent of the stepped balloon has made it possible to have less balloon material outside of the stent. Although this technique is advantageous for its reduction of vessel injury, it actually makes the crimped stent edge more exposed (unless the balloon material is intentionally pre-expanded). The endcaps of the present invention address this problem by capping the ends of the stent. This capping also serves to hold the stent on the balloon before inflation. The endcaps further serve to decrease the deflation time of the balloon and assist in the folding of the balloon upon deflation.

Referring now to FIGS. 2–9, in one embodiment endcaps 24a, 24b can be designed to be interdigitating with the stent. The terms "interdigitate," "interdigitates," and "interdigitating" as used herein refer to any degree of interdigitation from slight interdigitation to great interdigitation where the endcaps follow the shape of the stent. This design provides maximum contact area and facilitates the spreading out of transmitted compressive forces. This design also provides for maximum protection of the stent from passing objects. Alternatively, the endcaps can be designed to have relatively smooth first ends 28 and be non-interdigitating with the ends of the stent. Endcaps that are interdigitating can be embodied in various configurations. For example, the first ends may possess serpentine or undulating patterns.

Generally speaking, endcaps 24a, 24b can be formed separately by injection molding, casting, machining or other methods known to those skilled in the art for fabricating small elastomeric parts. The endcaps can be formed by in situ polymerization, crosslinking or setting of a flowable precursor. The endcaps may be sculpted if desired. In one embodiment, a polymer in liquid or gel form may be applied directly to the mounted stent and formed in situ. Some examples of materials that can be used to construct the endcaps include polyurethanes, polyetherurethanes, polyesterurethanes, silicone, C-flex thermoplastic elastomer, Pebax (polyether-amide thermoplastic elastomer), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, Kraton (a family of elastomers composed of styrene, ethylene, propylene, butadiene and isoprene) and Hytrel (polyester thermoplastic elastomer).

In one embodiment, a curing process may be used on a curable polymer, such as ultraviolet curing or other suitable processes. The endcaps can be mounted on catheter 12 by using adhesive to attach them to the catheter. In another embodiment, the encaps can be formed out of an elastomeric tubing by machining the tubing. It is also envisioned that the encaps can be formed integrally with the catheter.

In one method of forming an endcap, a liquid is introduced onto the expandable member distal to the stent. The liquid is allowed to harden such that an interdigitating endcap is formed. The liquid can include a thermoset (or liquid precursor) or a molten thermoplastic. It is envisioned that a tubular sleeve can be utilized with this method. The sleeve can be mounted on the stent such that the sleeve extends distally from the stent forming a space between the sleeve and a portion of the expandable member distal to the stent. The liquid is introduced onto the expandable member and into the space between the sleeve and the expandable member. The liquid is allowed to harden and the sleeve is removed. Ultraviolet curing can be utilized in conjunction with this method.

In an alternate method, a tapered cylindrical mold can be utilized. A liquid, which can be a thermoset or molten thermoplastic, is introduced into the mold and allowed to harden such that an endcap is formed. The endcap can then be applied to the catheter distal to the stent with an adhesive.

In further keeping with the invention, a guide catheter is provided, as is known in the art, that has a proximal end and a distal end, and is formed with a lumen for receiving the delivery assembly therein. The guide catheter facilitates the advancement of the stent delivery system through a patient's vasculature and has a diameter large enough to allow free longitudinal movement of the stent deployment assembly therein.

In operation, the guide catheter is percutaneously introduced into the cardiovascular system of a patient through, for instance, the femoral artery, and is advanced therein until the distal tip thereof is just proximal of the vessel site to be treated. The stent deployment system is introduced through the guide catheter with guide wire 18 slidably disposed within the lumen of delivery catheter 12. Upon reaching the distal end of the guide catheter, the guide wire is extended out from catheter 12 and is advanced to the target site. Thereafter, catheter 12 and stent 26 are advanced over the guide wire, such as by manipulating a manipulator handle or other appropriate device, until the stent is positioned at the desired location.

To deploy stent 26, the physician, while using a fluoroscope to view the treated site, injects a radiopaque contrast media through inflation lumen 22, as is known in the art. The expandable member 14 expands as a result. The expansion of the expandable member causes the stent to expand. The endcaps 24a, 24b simultaneously expand with the stent as the expandable member expands. The endcaps slide axially away from the stent as the expandable member (the balloon) continues to expand. The endcaps slide down the shoulders of the balloon as the balloon continues to expand. Beforehand, a mold release compound can be applied to the ends of the stent and the balloon shoulders to reduce sticking and friction. Additionally, a lubricous coating can be applied to the outside of the endcaps and outside the catheter for easy sliding within the vessel and the guide.

Finally, stent 26 expands against the vessel wall. The balloon 14 is then deflated. The deflation process normally can take a significant amount of time and this can be dangerous to the patient as blood flow is restricted while the balloon is expanded. The endcaps of the present invention, due to their memory, facilitate rapid deflation of the balloon. The endcaps constrict to approximately their original pre-expanded condition as the balloon is deflated. The delivery system is withdrawn from the patient's body after the stent has fully deployed, with the stent remaining in the vessel lumen to maintain the patency of the treated vessel.

From the foregoing, it will be appreciated that stent delivery system 10 of the present invention allows stents to be deployed while preventing the stents from sliding off of expandable member 14 or catching on objects. The invention is made of materials commonly found in the industry and is simple to use and easy to manufacture. The significance of the invention includes the fact that it can improve stent retention without compromising the balloon function, affecting the delivery system flexibility or increasing the system profile. Looking ahead, future stents will be lower in profile. Since the stents will still be required to expand to the same diameters as required presently, one consequence is that when crimped the stents will have little or no space between the struts. One means of increasing the coefficient of friction between the stent and balloon is to have the crimped stent press into the balloon with some balloon material protruding between the struts. With stents that are solid jackets of metal, this is no longer possible. Furthermore, it is expected that future stents will exhibit thinner struts, thus reducing the crimping force that the stent can exert on the balloon. This could further reduce stent retention. The present invention addresses these problems, as has been shown.

While the invention herein has been illustrated and described in terms of a stent deployment system with novel endcaps, it will be apparent to those skilled in the art that the invention can be used in other instances. Other modifications and improvements may be made without departing from the scope of the invention.

What is claimed:

1. A stent deployment assembly for delivery of a stent within a body lumen, comprising:

a catheter having a proximal end and a distal end;

an expandable member on the distal end of the catheter;

a stent crimped on the expandable member;

an endcap in apposition with an end of the stent, the endcap in the shape of a tapered member including a first end and a second end, the first end and the second end each having an aperture therethrough;

the endcap having a pre-expanded condition and an expanded condition;

the first end of the endcap positioned against an end of the stent when the endcap is in the pre-expanded condition;

the first end of the endcap interdigitates with respect to an end of the stent; and wherein the expandable member contacts the catheter at a weld joint and the endcap is attached to the catheter proximate the weld joint.

2. A stent deployment assembly for delivery of a stent within a body lumen, comprising:

a catheter having a proximal end and a distal end;

an expandable member on the distal end of the catheter;

a stent crimped on the expandable member;

an endcap in apposition with an end of the stent, the endcap in the shape of a tapered member including a first end and a second end, the first end and the second end each having an aperture therethrough;

the endcap having a pre-expanded condition and an expanded condition;

the first end of the endcap positioned against an end of the stent when the endcap is in the pre-expanded condition;

the first end of the endcap interdigitates with respect to an end of the stent; and wherein the expandable member contacts the endcap at a weld joint and the endcap is attached to the catheter at the weld joint.

* * * * *